(12) United States Patent
Lampotang et al.

(10) Patent No.: US 7,820,108 B2
(45) Date of Patent: Oct. 26, 2010

(54) MARKER DETECTION METHOD AND APPARATUS TO MONITOR DRUG COMPLIANCE

(75) Inventors: Samsun Lampotang, Gainesville, FL (US); Richard J. Melker, Gainesville, FL (US); David N. Silverman, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 985 days.

(21) Appl. No.: 10/722,620

(22) Filed: Nov. 26, 2003

(65) Prior Publication Data

US 2004/0081587 A1    Apr. 29, 2004

Related U.S. Application Data

(63) Continuation of application No. 09/708,789, filed on Nov. 8, 2000, now abandoned.

(60) Provisional application No. 60/164,250, filed on Nov. 8, 1999.

(51) Int. Cl.
*G01N 1/22* (2006.01)
*G01N 37/00* (2006.01)
*G01N 33/497* (2006.01)
*G01N 31/00* (2006.01)
*G01N 7/00* (2006.01)

(52) U.S. Cl. ............ 422/84; 422/83; 422/85; 422/86; 436/13; 436/56; 436/164; 436/171; 73/23.2; 73/23.3; 73/23.34

(58) Field of Classification Search ........... 422/84; 73/23.3; 436/13
See application file for complete search history.

(56) References Cited

U.S. PATENT DOCUMENTS 3,567,029 A    3/1971    Quame
3,608,546 A    9/1971    Shinn (Continued)

FOREIGN PATENT DOCUMENTS

DE    19607646 A1    9/1997

(Continued)

OTHER PUBLICATIONS

Arvanitakis, C. et al., "Lactase Deficiency- a Comparative Study of Diagnostic Methods", *The American Journal of Clinical Nutrition*, Oct. 30, 1977, pp. 1597-1602, vol. 10.

(Continued)

*Primary Examiner*—Jill Warden
*Assistant Examiner*—Neil Turk
(74) *Attorney, Agent, or Firm*—Timothy H. Van Dyke; Beusse Wolter Sanks Mora & Maire (57) ABSTRACT

The present invention includes a method and apparatus for monitoring drug compliance by detecting markers, such as odors, upon exhalation by a patient after medication is taken, wherein such markers result either directly from the medication itself or from an additive combined with the medication. In the case of olfactory markers, the invention preferably utilizes electronic sensor technology, such as the commercial devices referred to as "artificial noses" or "electronic noses," to non-invasively monitor compliance. The invention further includes a reporting system capable of tracking compliance (remote or proximate) and providing the necessary alerts.

32 Claims, 3 Drawing Sheets

Patient Compliance Monitoring System
Overview

Step 1
Patient takes Medication

Step 2
Patient exhales into Feedback System

PCMS includes marker compound included in medication that is exhaled into detection system for accurate and reliable monitoring off-site

U.S. PATENT DOCUMENTS

| | | | |
|---|---|---|---|
| 3,649,199 A | 3/1972 | Littlejohn | |
| 3,792,272 A | 2/1974 | Harte et al. | |
| 3,877,291 A | 4/1975 | Hoppesch et al. | |
| 3,951,607 A | 4/1976 | Fraser | |
| 3,955,926 A | 5/1976 | Fischer | |
| 4,150,670 A | 4/1979 | Jewett et al. | |
| 4,202,352 A | 5/1980 | Osborn | |
| 4,215,409 A | 7/1980 | Strowe | |
| 4,312,228 A | 1/1982 | Wohltjen | |
| 4,314,564 A | 2/1982 | Albarda | |
| 4,334,540 A | 6/1982 | Preti et al. | |
| 4,346,584 A | 8/1982 | Boehringer | |
| 4,349,626 A | 9/1982 | Labows et al. | |
| 4,353,869 A * | 10/1982 | Guth | 422/102 |
| 4,361,026 A | 11/1982 | Muller et al. | |
| 4,399,686 A | 8/1983 | Kindlund et al. | |
| 4,432,226 A | 2/1984 | Dempster | |
| 4,456,014 A | 6/1984 | Buck et al. | |
| 4,534,360 A | 8/1985 | Williams | |
| 4,734,777 A | 3/1988 | Okino et al. | |
| 4,735,777 A | 4/1988 | Mitsui et al. | |
| 4,762,719 A * | 8/1988 | Forester | 424/440 |
| 4,772,559 A | 9/1988 | Preti et al. | |
| 4,796,639 A | 1/1989 | Snow et al. | |
| 4,868,545 A | 9/1989 | Jones | |
| 4,895,017 A | 1/1990 | Pyke et al. | |
| 4,938,928 A | 7/1990 | Koda et al. | |
| 4,992,244 A | 2/1991 | Grate | |
| 5,003,985 A | 4/1991 | White et al. | |
| 5,034,192 A | 7/1991 | Wrighton et al. | |
| 5,042,501 A | 8/1991 | Kenny et al. | |
| 5,060,506 A | 10/1991 | Douglas | |
| 5,071,770 A | 12/1991 | Kolesar, Jr. | |
| 5,081,871 A | 1/1992 | Glaser | |
| 5,082,630 A | 1/1992 | Partin et al. | |
| 5,094,235 A | 3/1992 | Westenskow et al. | |
| 5,111,827 A | 5/1992 | Rantala | |
| 5,137,692 A | 8/1992 | Fritz | |
| 5,145,645 A | 9/1992 | Zakin et al. | |
| 5,167,972 A | 12/1992 | Greenberg et al. | |
| 5,179,027 A | 1/1993 | Fisher | |
| 5,220,919 A * | 6/1993 | Phillips et al. | 600/345 |
| 5,252,292 A | 10/1993 | Hirata et al. | |
| 5,296,706 A | 3/1994 | Braig et al. | |
| 5,303,575 A | 4/1994 | Brown et al. | |
| 5,317,156 A | 5/1994 | Cooper et al. | |
| 5,325,704 A | 7/1994 | Mariani et al. | |
| 5,351,522 A | 10/1994 | Lura | |
| 5,361,771 A | 11/1994 | Craine et al. | |
| 5,409,839 A | 4/1995 | Balestrieri et al. | |
| 5,425,374 A | 6/1995 | Ueda et al. | |
| 5,447,165 A | 9/1995 | Gustafsson | |
| 5,453,359 A | 9/1995 | Gargan et al. | |
| 5,465,608 A | 11/1995 | Lokshin et al. | |
| 5,466,700 A | 11/1995 | Batenhorst et al. | |
| 5,482,601 A | 1/1996 | Ohshima et al. | |
| 5,495,744 A | 3/1996 | Ueda et al. | |
| 5,501,212 A | 3/1996 | Psaros | |
| 5,528,924 A | 6/1996 | Wajid et al. | |
| 5,547,878 A | 8/1996 | Kell | |
| 5,558,083 A | 9/1996 | Bathe et al. | |
| 5,560,352 A | 10/1996 | Heim et al. | |
| 5,571,401 A | 11/1996 | Lewis et al. | |
| 5,573,005 A | 11/1996 | Ueda et al. | |
| 5,573,955 A | 11/1996 | Khanna et al. | |
| 5,605,612 A | 2/1997 | Park et al. | |
| 5,634,517 A | 6/1997 | Linden et al. | |
| 5,645,072 A | 7/1997 | Thrall et al. | |
| 5,652,146 A * | 7/1997 | Kell | 436/111 |
| 5,716,852 A | 2/1998 | Yager et al. | |
| 5,756,879 A | 5/1998 | Yamagishi et al. | |
| 5,771,890 A | 6/1998 | Tamada | |
| 5,776,783 A | 7/1998 | Kell | |
| 5,783,154 A | 7/1998 | Althainz et al. | |
| 5,783,449 A | 7/1998 | Kuznetsov | |
| 5,795,787 A | 8/1998 | Silkoff et al. | |
| 5,801,297 A | 9/1998 | Mifsud et al. | |
| 5,826,577 A | 10/1998 | Perroz et al. | |
| 5,830,412 A | 11/1998 | Kimura et al. | |
| 5,861,254 A | 1/1999 | Schneider et al. | |
| 5,866,434 A | 2/1999 | Massey et al. | |
| 5,891,398 A | 4/1999 | Lewis et al. | |
| 5,900,552 A | 5/1999 | Chu et al. | |
| 5,918,257 A | 6/1999 | Mifsud et al. | |
| 5,925,014 A | 7/1999 | Teeple, Jr. | |
| 5,928,167 A | 7/1999 | Wagner et al. | |
| 5,932,877 A | 8/1999 | Braig et al. | |
| 5,945,069 A | 8/1999 | Buehler | |
| 5,950,630 A | 9/1999 | Portwood et al. | |
| 5,954,685 A | 9/1999 | Tierney | |
| 5,958,896 A | 9/1999 | Renshaw et al. | |
| 5,962,335 A | 10/1999 | Katzman | |
| 5,971,937 A | 10/1999 | Ekstrom | |
| 5,996,586 A | 12/1999 | Phillips | |
| 6,007,775 A | 12/1999 | Yager | |
| 6,010,459 A | 1/2000 | Silkoff et al. | |
| 6,025,200 A | 2/2000 | Kaish et al. | |
| 6,057,162 A | 5/2000 | Rounbehler et al. | |
| 6,063,243 A | 5/2000 | Zettl et al. | |
| 6,067,167 A | 5/2000 | Atkinson et al. | |
| 6,074,345 A | 6/2000 | Van Oostrom et al. | |
| 6,085,576 A | 7/2000 | Sunshine et al. | |
| 6,094,681 A | 7/2000 | Shaffer et al. | |
| 6,097,485 A | 8/2000 | Lievan | |
| 6,120,443 A | 9/2000 | Cohen-Laroque | |
| 6,131,571 A | 10/2000 | Lampotang et al. | |
| 6,136,801 A | 10/2000 | Kell | |
| 6,153,147 A | 11/2000 | Craig | |
| 6,180,414 B1 | 1/2001 | Katzman | |
| 6,186,977 B1 | 2/2001 | Andrews et al. | |
| 6,190,858 B1 | 2/2001 | Persaud et al. | |
| 6,203,814 B1 | 3/2001 | Fisher et al. | |
| 6,216,690 B1 | 4/2001 | Keitel et al. | |
| 6,221,026 B1 | 4/2001 | Phillips | |
| 6,234,006 B1 | 5/2001 | Sunshine et al. | |
| 6,237,397 B1 | 5/2001 | Shinar et al. | |
| 6,244,096 B1 | 6/2001 | Lewis et al. | |
| 6,248,078 B1 | 6/2001 | Risby et al. | |
| 6,251,082 B1 | 6/2001 | Rayburn | |
| 6,261,783 B1 | 7/2001 | Jayasena et al. | |
| 6,264,913 B1 | 7/2001 | Wagner | |
| 6,277,081 B1 | 8/2001 | Susi et al. | |
| 6,283,953 B1 | 9/2001 | Ayer et al. | |
| 6,303,316 B1 | 10/2001 | Kiel et al. | |
| 6,305,212 B1 | 10/2001 | Drzewiecki | |
| 6,312,390 B1 | 11/2001 | Phillips | |
| 6,319,724 B1 | 11/2001 | Lewis et al. | |
| 6,328,708 B1 | 12/2001 | Georgieff | |
| 6,341,520 B1 | 1/2002 | Satoh et al. | |
| 6,363,772 B1 | 4/2002 | Berry | |
| 6,387,329 B1 | 5/2002 | Lewis et al. | |
| 6,399,302 B1 | 6/2002 | Lannigan et al. | |
| 6,416,479 B1 | 7/2002 | Seidman | |
| 6,455,319 B1 | 9/2002 | Lewis et al. | |
| 6,467,333 B2 | 10/2002 | Lewis et al. | |
| 6,479,019 B1 | 11/2002 | Goldstein et al. | |
| 6,495,824 B1 | 12/2002 | Atkinson | |
| 6,511,453 B2 | 1/2003 | Georgieff | |
| 6,558,626 B1 | 5/2003 | Aker et al. | |
| 6,589,727 B1 | 7/2003 | Klenerman et al. | |
| 6,597,438 B1 | 7/2003 | Cabuz et al. | |
| 6,598,459 B1 | 7/2003 | Fu | |
| 6,599,253 B1 | 7/2003 | Baum et al. | |
| 6,599,281 B1 | 7/2003 | Struys et al. | |

| | | |
|---|---|---|
| 6,620,800 B1 | 9/2003 | Roberts, II |
| 6,631,333 B1 | 10/2003 | Lewis et al. |
| 6,680,377 B1 | 1/2004 | Stanton et al. |
| 6,727,075 B2 | 4/2004 | Fitzgerald et al. |
| 6,755,783 B2 | 6/2004 | Cosentino et al. |
| 2001/0021815 A1 | 9/2001 | Katzman et al. |
| 2001/0041366 A1 | 11/2001 | Lewis et al. |
| 2001/0046674 A1 | 11/2001 | Ellington |
| 2001/0050228 A1 | 12/2001 | Jaeger |
| 2001/0055544 A1 | 12/2001 | Copp |
| 2002/0007249 A1 | 1/2002 | Cranley et al. |
| 2002/0007687 A1 | 1/2002 | Zimmermann et al. |
| 2002/0014236 A1 | 2/2002 | Dittmann et al. |
| 2002/0017300 A1 | 2/2002 | Hickle et al. |
| 2002/0034757 A1 | 3/2002 | Cubicciotti |
| 2002/0068295 A1 | 6/2002 | Madou et al. |
| 2002/0173729 A1 | 11/2002 | Viertio-Oja et al. |
| 2002/0177232 A1 | 11/2002 | Melker et al. |
| 2003/0004426 A1 | 1/2003 | Melker et al. |
| 2003/0008407 A1 | 1/2003 | Fu |
| 2003/0059820 A1 | 3/2003 | Vo-Dinh |
| 2003/0087239 A1 | 5/2003 | Stanton et al. |
| 2003/0119065 A1 | 6/2003 | Lin et al. |
| 2003/0139681 A1 | 7/2003 | Melker et al. |
| 2003/0185760 A1 | 10/2003 | Lanza et al. |
| 2003/0216660 A1 | 11/2003 | Ben-Oren et al. |
| 2004/0027246 A1 | 2/2004 | Aguglia |
| 2004/0101477 A1 | 5/2004 | Leyland-Jones |
| 2005/0037374 A1 | 2/2005 | Melker et al. |
| 2005/0065446 A1 | 3/2005 | Talton |

FOREIGN PATENT DOCUMENTS

| | | |
|---|---|---|
| DE | 29902593 | 8/1999 |
| EP | 0 370 151 A1 | 5/1990 |
| EP | 0 979 997 A1 | 2/2000 |
| GB | 829409 A | 3/1960 |
| GB | 2 309 166 A | 7/1997 |
| GB | 2309166 | 7/1997 |
| GB | 2 329 245 A | 3/1999 |
| JP | 08313407 A | 11/1996 |
| JP | 09196915 A | 7/1997 |
| RU | 2104535 C1 | 2/1998 |
| WO | WO 87/02773 A1 | 5/1987 |
| WO | WO 92/10749 A1 | 6/1992 |
| WO | WO 95/08113 A1 | 3/1995 |
| WO | WO 95/31718 A1 | 11/1995 |
| WO | WO 9839470 A1 * | 9/1998 |
| WO | WO 98/57145 A1 | 12/1998 |
| WO | 9912471 | 3/1999 |
| WO | WO 99/12471 A3 | 3/1999 |
| WO | WO 99/66304 A1 | 12/1999 |
| WO | WO 00/25108 A1 | 5/2000 |
| WO | WO 00/67820 A1 | 11/2000 |
| WO | WO 00/79243 A1 | 12/2000 |
| WO | WO 01/34024 A1 | 5/2001 |
| WO | WO 01/93743 A2 | 12/2001 |
| WO | WO 02/079514 | 10/2002 |
| WO | WO 03/016901 A1 | 2/2003 |
| WO | WO 03/045473 A1 | 6/2003 |
| WO | WO 2004/037316 A2 | 5/2004 |
| WO | WO 2004/065404 A1 | 8/2004 |
| WO | WO 2005/033707 A1 | 4/2005 |

OTHER PUBLICATIONS

Barkley, J. et al., "Gas Chromatography Mass Spectrometry Computer Analysis of Volatile Halogenated Hydrocarbons in Man and His Environment- A Multimedia Environmental Study", *Biomedical Mass Spectrometry*, 1980, pp. 139-147, vol. 7, No. 4, Heyden & Son Ltd.

Caspary, W. F., "Breath Tests", *Clinics in Gastroenterology*, May 1978, pp. 351-374, vol. 7, No. 2.

Conkle, J. P. et al., "Trace Composition of Human Respiratory Gas", *Arch Environ Health*, Jun. 1975, pp. 290-295, vol. 30.

Gage, J.C. et al., "A Method for the Determination of Low Concentrations of Organic Vapours in Air and Exhaled Breath", *Ann. occup. Hyg.*, 1977, pp. 127-134, vol. 20, Pergamon Press, Great Britain.

Krotoszynski, B. et al., "Characterization of Human Expired Air: A Promising Investigative and Diagnostic Technique", *J. Chromatogr. Sci.*, Jul. 1977, pp. 239-244, vol. 15.

Maugh, T.H., "Separations by MS Speed Up, Simplify Analysis", *Science, New Series*, Aug. 8, 1980, pp. 675-677, vol. 209, No. 4457, American Association for the Advancement of Science.

McLafferty, F., "Tandem Mass Spectrometry", *Science, New Series*, Oct. 16, 1981, pp. 280-287, vol. 214, No. 4518, American Association for the Advancement of Science.

O'Neill et al., "A Computerized Classification Technique for Screening for the Presence of Breath Biomarkers on Lung Cancer", *Clinical Chemistry*, 1988, pp. 1613-1618, vol. 34, No. 8.

Phillips, M., "Breath Tests in Medicine", *Scientific American*, Jul. 1992, pp. 74-79.

Schwabe, A.D. et al., "Breath Tests for the Detection of Fat Malabsorbtion", *Gastroenterology*, Jan. 1979, pp. 216-218, vol. 76, No. 1.

Yost, R.A. et al., "Triple Quadruple Mass Spectrometry for Direct Mixture and Analysis and Structure Elucidation", *Analytical Chemistry*, Oct. 1979, pp. 1251-1264, vol. 51, No. 12.

U.S. Appl. No. 09/708,789, filed Nov. 8, 2000, Lampotang et al.

Ballantine, D. S. et al., "Surface Acoustic Wave Devices for Chemical Analysis," *Anal. Chem.* (1989), vol. 61, No. 11, pp. 704A-712A.

Brody, E. N. et al., "Aptamers as Therapeutic and Diagnostic Agents," *Reviews in Molecular Biotechnology* (2000), vol. 74, pp. 5-13.

Brody et al. "The use of Aptamers in Large Arrays for Molecular Diagnostics," *Molecular Diagnosis* (1999), vol. 4, No. 4, pp. 381-388.

Chandiok, S. et al. "Screening for Bacterial Vaginosis: A Novel Application of Artificial Nose Technology," *Journal of Clinical Pathology* (1997), vol. 50, pp. 790-791.

Dickinson, T. A. et al., "Current Trends in 'Artificial-Nose' Technology," *Tib Tech*, 1998, 16:250-258.

Fang, M. et al. "Detection of Organic Chemicals by SAW Sensor Array," *Sensors and Actuators* (1999), vol. B56, pp. 155-157.

Fisher et al. "A man-portable chemical sniffer utilizing Novel Fluorescent polymers for detection of ultra-trace concentrations of explosives emanating from landmines," *Nomadics Inc.* (2000), pp. 1-10.

Frauendorf, A. et al., "Detection of Small Organic Analytes by Fluorescing Molecular Switches," *Bioorganic & Medicinal Chemistry 9*, (2001), pp. 2521-2524.

Fujita et. al., "A Simple Method for Dectecting Plasma Propofol,"*Anesth. Analog.*, 2000, 90:1452-1454.

Ganga-Zandzou, P.S. et al. "A 13C-urea breath test in children with *Helicobacter pylori* infection: validity of the use of a mask to collect exhaled breath sample," *Acta. Paediatr*. (2001), vol. 90, pp. 232-233.

Grate, JW et al. "Determination of Partition Coefficients from Surface Acoustic Wave Vapor Senor Responses and Correlation with Gas-Liquid Chromatographic Partition Coefficients," *Anal. Chem.* (1998), vol. 60, pp. 869-875.

Groves, W. et al. "Analyzing organic vapors in exhaled breath using a surface acoustic wave sensor array with preconcentration: Selection and characterization of the preconcentrator adsorbent," *Analytica Chimica Acta* (1998), vol. 371, pp. 131-143.

Hammon III, W. S. et al., "Forensic GPR: Finite-Difference Simulations of Responses From Buried Human Remains," *Journal of Applied Geophysics*, (2000), 45:171-186.

Hanson III, C.W. et al. "The use of a novel 'Electronic Nose' to diagnose the presence of intrapulmonary infection," *Anesthesiology* (1997), vol. 87, No. 3A, abstract A269.

Hong, C. et al., "Carbon Nanotube-Enhanced Electrochemical DNA Biosensor for DNA Hybridization Detection" (2003), *Anal. Bioanal. Chem.*, 375:287-293.

Huang et. al., "Depth of Anesthesia Estimating & Propofol Delivery System," Aug. 1, 1996, http://www.rpi.edu/~royr/roy_descpt.html.

Jayasena, "Aptamers: An Emerging Class of Molecules That Rival Antibodies in Diagnostics," *Clinical Chemistry*, 1999, 45(9):1628-1650.

Kenny, "Target-Controlled Infusions -Pharmacokinetic and Pharmacodynamic Variations," http://www.anaesthesiologie.med.uni-erlanglen.de/esctaic97/a_kenny.htm, Jun. 12, 2001.

Kuipers et al., "First-pass Lung Uptake and Pulmonary Clearance of Propofol," *Anesthesiology*, (1999), 91:1780-1787.

Liebich et al. "Volatile Substances in Blood Serum: a Profile Analysis and Quantitative Determination," *Journal of Chromatography* (1977), vol. 142, pp. 505-516.

Miller III, E. R. et al., "Association Between Cigarette Smoking and Lipid Peroxidation in a Controlled Feeding Study," *Circulation*, (1997), 96(4):1097-1101.

Mueller et al. "Experience in mass spectrometric identification in acute poisoning," *Beitr. Diagn. Ther, Akuter. Intox., Vortr. Symp. 4$^{th}$* (1982), pp. 126-134, Abstract Only.

Pantarotto D. et al., "Synthesis, Structural Characterization, and Immunological Properties of Carbon Nanotubes Functionalized with Peptides" (2003), *J. Am. Chem. Soc.*, 125:6160-6164.

Parry, A.D. et al. "Leg Ulcer Odour Detection Identifies β-haemolytic Streptococcal Infection," *Journal of Wound Care* (1995), vol. 4, No. 9, pp. 404-406.

Pavlou and Turner. "Sniffing out the truth: Clinical Diagnosis Using the Electronic Nose," Clin. Chem. Lab. Med. (2000), vol. 38, No. 2, pp. 99-112.

Perri, F. "Diagnosis of *Helicobacter pylori* infection: which is best? The urea breath test," *Dig. Liver. Dis.* (2000), vol. 32, Supp. 3, pp. S196-S198.

Phillips, M., "Breath Tests in Medicine," *Scientific American*, 1992, pp. 52-57.

Pilar Kraman, "Prescription Drug Diversion," *Trends Alert* provided by the Council of State Government at www.csg.ord (Apr. 2004).

Rogers et al. "Fiber-optic biosensors based on total internal-reflection fluorescence," *American Chemical Society* (1992), Ch. 13, pp. 165-173.

Stojanovic, M. N. et al., "Aptamer-Based Folding Fluorescent Sensor for Cocaine," *J. Am. Chem. Soc.*, 123:4928-4931, (2001).

Stuart, B. H. et al., "Studies of Adipocere Using Diffuse Reflectance Infrared Spectroscopy," *Vibrational Spectroscopy*, 24:233-242, (2000).

Stubbs, D. D. et al., "Investigation of Cocaine Plumes Using Surface Acoustic Wave Immunoassay Sensors," *Anal. Chem.*, 75:6231-6235, (2003).

Tracqui, A. et al. "Systematic Toxicological Analysis Using HPLC/DAD," *Journal of Forensic Sciences* (1995), vol. 40, No. 2, pp. 254-262.

U.S. Food and Drug Administration, "FDA White Paper, Protecting the Public Health: FDA Pursues and Aggressive Enforcement Strategy," www.fda.gov/oc/whitepapers/enforce.html (Jun. 30, 2003).

U.S. Food and Drug Administration, "New FDA Initiative to Combat Counterfeit Drugs," www.fda.gov/oc/initiatives/counterfeit/backgrounder.html (Jul. 2, 2004).

United States Department of Justice, "Review of the Drug Enforcement Administration's (DEA) Control of the Diversion of Controlled Pharmaceuticals," Report No. I-2002-010 www.usdoj.gov/oig/inspection/DEA/0210/background.htm (Sep. 2002).

Wohltjen, H. et al. "Vapor Detection with Surface Acoustic Wave Microsensors," *Chemical Sensors and Microinstrumentation* (1989), pp. 157-175.

Vass, A., "Beyond the Grave—Understanding Human Decomposition," *Microbiology Today*, Nov. 2001, 28:190-192.

Vass, A. et al., "Decomposition Chemistry of Human Remains: A New Methodology for Determining the Postmortem Interval," *J. Forensic Sci.*, (2002), 47(3):542-553.

Vass, A. et al., "Detection of Buried Human Remains Using Bioreporter Fluorescence," U.S. Dept. of Energy Report, Y/NSP-726 (2001).

\* cited by examiner

FIG. 1

Patient Compliance Monitoring System
Overview

PCMS includes marker compound included in medication that is exhaled into detection system for accurate and reliable monitoring off-site

FIG. 2

Patient Compliance Monitoring System
Step 1 - Medication is taken, releasing Marker Compound Marker compound is released by dosage form for detection

MARKER DETECTION METHOD AND APPARATUS TO MONITOR DRUG COMPLIANCE

CROSS-REFERENCE TO A RELATED APPLICATION

This application is a continuation application of U.S. Ser. No. 09/708,789, filed Nov. 8, 2000 now abandoned, and claims the benefit of U.S. Provisional Application No. 60/164,250, filed Nov. 8, 1999, which is hereby incorporated by reference herein in its entirety.

FIELD OF INVENTION

The present invention relates to marker detection, in the form of odors or the like, to monitor drug compliance, and, more particularly, to a method and apparatus for the detection of markers wherein such markers are detectable either directly from the medication itself or from an additive combined with the medication and are detected upon exhalation after medication is taken by a patient.

BACKGROUND INFORMATION

Non-compliance of patients to drug regimens prescribed by their physicians results in excessive healthcare costs estimated to be around $100 billion per year through lost work days, increased cost of medical care, higher complication rates, as well as drug wastage. Non-compliance refers to the failure to take the prescribed dosage at the prescribed time which results in undermedication or overmedication. In a survey of 57 non-compliance studies, non-compliance ranged from 15% to as high as 95% in all study populations, regardless of medications, patient population characteristics, drug being delivered or study methodology [Greenberg R N: Overview of patient compliance with medication dosing: A literature review. *Clinical Therapeutics*, 6(5):592-599, 1984].

The sub-optimal rates of compliance reported by various studies becomes of even greater concern as the American populace ages and becomes more dependent on drugs to fight the illnesses accompanying old age. By 2025, over 17% of the US population will be over 65 [Bell J A, May F E, Stewart R B: Clinical research in the elderly: Ethical and methodological considerations. *Drug Intelligence and Clinical Pharmacy*, 21: 1002-1007, 1987] and senior citizens take, on average, over three times as many drugs compared to the under 65 population [Cosgrove R: Understanding drug abuse in the elderly. *Midwife, Health Visitor & Community Nursing* 24(6): 222-223, 1988]. The forgetfulness that sometimes accompanies old age also makes it even more urgent to devise cost-effective methods of monitoring compliance on a large scale.

Further, non-compliance of patients with communicable diseases (e.g., tuberculosis and related opportunistic infections) costs the public health authorities millions of dollars annually and increases the likelihood of drug-resistance, with the potential for widespread dissemination of drug-resistant pathogens resulting in epidemics.

A cost-effective, but difficult to administer, program has been developed in seven locations around the nation to combat this serious threat to the American populace. It involves direct observation of all drug delivery by trained professionals (directly observed therapy: DOT) but is impractical for large scale implementation. Many techniques are also invasive, e.g., blood sampling.

Accordingly, there is a need in the art for a method to improve drug compliance which provides simple monitoring of medication dosing which is non-invasive, intuitive and sanitary.

BRIEF SUMMARY OF THE INVENTION

The present invention solves the needs in the art by providing a method and apparatus for monitoring drug compliance by detecting markers, such as odors, upon exhalation by a patient after medication is taken, wherein such markers result either directly from the medication itself or from an additive combined with the medication. In the case of olfactory markers, the invention preferably utilizes electronic sensor technology, such as the commercial devices referred to as "artificial noses" or "electronic noses," to non-invasively monitor compliance. The invention further includes a reporting system capable of tracking compliance (remote or proximate) and providing the necessary alerts.

Therefore, it is an object of the present invention to detect marker substances as a measure of patient compliance by methods including, but not limited to, sensor technology (e.g., silicon chip technology) to non-invasively monitor compliance of patients to prescribed drug regimens.

It is a further object of the present invention to provide a reporting system capable of tracking compliance and alerting patients, healthcare personnel, and/or in some instances health officials of non-compliance.

The invention will now be described, by way of example and not by way of limitation, with reference to the accompanying sheets of drawings and other objects, features and advantages of the invention will be apparent from this detailed disclosure and from the appended claims. All patents, patent applications, provisional applications, and publications referred to or cited herein, or from which a claim for benefit of priority has been made, are incorporated by reference in their entirety to the extent they are not inconsistent with the explicit teachings of this specification.

DETAILED DESCRIPTION OF THE INVENTION

The present invention provides a method and apparatus for monitoring drug compliance by detecting markers released for detection upon exhalation after medication is taken by a patient. The detected markers are derived either directly from the medication itself or from a novel additive combined with the medication (referred to herein as "markers"). Such markers preferably include olfactory markers (odors) as well as other substances and compounds which may be detectable by various methods, as described in more detail herein. Throughout this disclosure the marker or marker substance is defined as a substance added to the medication or taken with the medication (i.e., as the coating on a pill) that is detected by means of its physical or chemical properties as an indication that the patient has taken the medication. This includes the use of the medication itself as its own marker. The marker substance is then detected by devices including but not limited to electronic noses, spectrophotometers to detect the marker's IR, UV, or visible absorbance or fluorescence, or mass spectrometers to detect the marker's characteristic mass display.

Gas Sensor Technology

The invention preferably utilizes gas sensor technology, such as the commercial devices referred to as "artificial noses" or "electronic noses," to non-invasively monitor compliance. Electronic noses have been used mostly in the food, wine and perfume industry where their sensitivity makes it possible to distinguish between grapefruit oil and orange oil and identify spoilage in perishable foods before the odor is evident to the human nose. There has been little medical-based research and application; however, recent examples demonstrate the power of this non-invasive technique. Electronic noses have determined the presence of bacterial infection in the lungs simply by analyzing the exhaled gases of patients for odors specific to particular bacteria [Hanson C W, Steinberger H A: The use of a novel electronic nose to diagnose the presence of intrapulmonary infection. *Anesthesiology*, V87, No. 3A, Abstract A269, September 1997]. Also a genitourinary clinic has utilized an electronic nose to screen for, and detect bacterial vaginosis, with a 94% success rate after training [Chandiok S, et al.: Screening for bacterial vaginosis: a novel application of artificial nose technology. Journal of Clinical Pathology, 50(9):790-1, 1997]. Specific bacterial species can also be identified with the electronic nose based on special odors produced by the organisms [Parry A D et al.: Leg ulcer odor detection identifies beta-haemolytic streptococcal infection. Journal of Wound Care, 4:404-406, 1995].

A number of patents which describe gas sensor technology include the following: U.S. Pat. No. 5,945,069 to Buchler, entitled "Gas sensor test chip"; U.S. Pat. No. 5,918,257 to Mifsud et al., entitled "Method and devices for the detection of odorous substances and applications"; U.S. Pat. No. 4,938,928 to Koda et al., entitled "Gas sensor"; U.S. Pat. No. 4,992,244 to Grate, entitled "Films of dithiolene complexes in gas-detecting microsensors"; U.S. Pat. No. 5,034,192 to Wrighton et al., entitled "Molecule-based microelectronic devices"; U.S. Pat. No. 5,071,770 to Kolesar, Jr., entitled "Method for gaseous component identification with #3 polymeric film"; U.S. Pat. No. 5,145,645 to Zakin et al., entitled "Conductive polymer selective species sensor"; U.S. Pat. No. 5,252,292 to Hirata et al., entitled "Ammonia sensor"; U.S. Pat. No. 5,605,612 to Park et al., entitled "Gas sensor and manufacturing method of the same"; U.S. Pat. No. 5,756,879 to Yamagishi et al., entitled "Volatile organic compound sensors"; U.S. Pat. No. 5,783,154 to Althainz et al., entitled "Sensor for reducing or oxidizing gases"; and U.S. Pat. No. 5,830,412 to Kimura et al., entitled "Sensor device, and disaster prevention system and electronic equipment each having sensor device incorporated therein," all of which are incorporated herein by reference in their entirety. Numerous methods for the detection of marker substances as known in the art may be utilized in the method of the present invention. For example, gas chromatography, which consists of a method of selective detection by separating the molecules of gas compositions, may be used as a way of monitoring markers. Another example of detection contemplated by the present invention includes transcutaneous/transdermal detection, such as that disclosed in U.S. Pat. No. 5,771,890 to Tamada and U.S. Pat. No. 5,954,685 to Tierney and the commercial device utilizing reverse iontophoresis sold by Cygnus, Inc. under the trademark "GlucoWatch®," the disclosures of which are incorporated herein by reference. Marker detection of the present invention through body fluids as known in the art such as sweat, saliva, urine, mucous, hair, nails, tears, and other bodily discharge are also contemplated herein (e.g., via ion exchange dipstick in combination with stain-producing agent, filtering fluids and treating with binding agent and reagents for color reaction, spectrophotometers, and the like). Recent developments in the field of detection of marker substances include, but are not limited to, semiconductive gas sensors, mass spectrometers, IR or UV or visible or fluorescence spectrophotometers. The marker substances change the electrical properties of the semiconductors by making their electrical resistance vary, and the measurement of these variations allows one to determine the concentration of marker substances. These methods and apparatus used for detecting marker substances use a relatively brief detection time, of around a few seconds, compared to those given by gas chromatography, which takes from several minutes to several hours. Other recent gas sensor technologies contemplated by the present invention include apparatus having conductive-polymer gas-sensors ("polymeric") and apparatus having surface-acoustic-wave (SAW) gas-sensors.

The conductive-polymer gas-sensors (also referred to as "chemoresistors") have a film made of a conductive polymer sensitive to the molecules of odorous substances. On contact with the molecules, the electric resistance of the sensors change and the measurement of the variation of this resistance enables the concentration of the odorous substances to be determined. An advantage of this type of sensor is that it functions at temperatures close to room temperature. One can also obtain, according to the chosen conductive polymer, different sensitivities for detecting different odorous substances.

Polymeric gas sensors can be built into an array of sensors, where each sensor is designed to respond differently to different gases and augment the selectivity of the odorous substances.

The surface-acoustic-wave (SAW) gas-sensors generally include a substrate with piezoelectric characteristics covered by a polymer coating which is able to selectively absorb the odorous substances. The variation of the resulting mass leads to a variation of its resonant frequency. This type of sensor allows for very good mass-volume measures of the odorous substances. In the SAW device, the substrate is used to propagate a surface acoustic wave between sets of interdigitated electrodes. The chemoselective material is coated on the surface of the transducer. When a chemical analyte interacts with a chemoselective material coated on the substrate, the interaction results in a change in the SAW properties such as the amplitude of velocity of the propagated wave. The detectable changes in the characteristics of the wave indicates the presence of the chemical analyte. SAW devices are described in numerous patents and publications, including U.S. Pat. No. 4,312,228 to Wohlijen and U.S. Pat. No. 4,895,017 to Pyke, and Groves W A, et al.: Analyzing organic vapors in exhaled breath using surface acoustic wave sensor array with preconcentration: Selection and characterization of the preconcentrator adsorbent, *Analytica Chimica Acta* 371 (1988) 131-143, all of which are incorporated herein by reference. Other types of chemical sensors known in the art that use chemoselective coatings applicable to the operation of the present invention include bulk acoustic wave (BAW) devices, plate acoustic wave devices, interdigitated microelectrode (IME) devices, and optical waveguide (OW) devices, electrochemical sensors, and electrically conducting sensors.

The operating performance of a chemical sensor that uses a chemoselective film coating is greatly affected by the thickness, uniformity and composition of the coating. For these biosensors, increasing the coating thickness, has a detrimental effect on the sensitivity. Only the portion of the coating immediately adjacent to the transducer substrate is sensed by the transducer. If the polymer coating is too thick, the sensitivity of the SAW device to record changes in frequency will be reduced. These outer layers of coating material compete for the analyte with the layers of coating being sensed and thus reduce the sensitivity of the biosensor. Uniformity of the coating is also a critical factor in the performance of a sensor that uses a chemoselective coating since changes in average surface area greatly effect the local vibrational signature of the SAW device. Therefore, films should be deposited that are flat to within 1 nm with a thickness of 15-25 nm. In this regard, it is important not only that the coating be uniform and reproducible from one device to another, so that a set of devices will all operate with the same sensitivity, but also that the coating on a single device be uniform across the active area of the substrate. If a coating is non-uniform, the response time to analyte exposure and the recovery time after analyte exposure are increased and the operating performance of the sensor is impaired. The thin areas of the coating respond more rapidly to an analyte than the thick areas. As a result, the sensor response signal takes longer to reach an equilibrium value, and the results are less accurate than they would be with a uniform coating.

Most current technologies for creating large area films of polymers and biomaterials involve the spinning, spraying, or dipping of a substrate into a solution of the macromolecule and a volatile solvent. These methods coat the entire substrate without selectivity and sometimes lead to solvent contamination and morphological inhomogeneities in the film due to non-uniform solvent evaporation. There are also techniques such as microcontact printing and hydrogel stamping that enable small areas of biomolecular and polymer monolayers to be patterned, but separate techniques like photolithography or chemical vapor deposition are needed to transform these films into microdevices. Other techniques such as thermal evaporation and pulsed laser ablation are limited to polymers that are stable and not denatured by vigorous thermal processes. More precise and accurate control over the thickness and uniformity of a film coating may be achieved by using pulsed laser deposition (PLD), a physical vapor deposition technique that has been developed recently for forming ceramic coatings on substrates. By this method, a target comprising the stoichiometric chemical composition of the material to be used for the coating is ablated by means of a pulsed laser, forming a plume of ablated material that becomes deposited on the substrate.

Polymer thin films, using a new laser based technique developed by researchers at the Naval Research Laboratory called Matrix Assisted Pulsed Laser Evaporation (MAPLE), have recently been shown to increase sensitivity and specificity of chemoselective Surface Acoustic Wave vapor sensors. A variation of this technique, Pulsed Laser Assisted Surface Functionalization (PLASF) is preferably used to design compound specific biosensor coatings with increased sensitivity for the present invention. PLASF produces similar thin films for sensor applications with bound receptors or antibodies for biosensor applications. By providing improved SAW biosensor response by eliminating film imperfections induced by solvent evaporation and detecting molecular attachments to specific antibodies, high sensitivity and specificity is possible.

Figure 1:
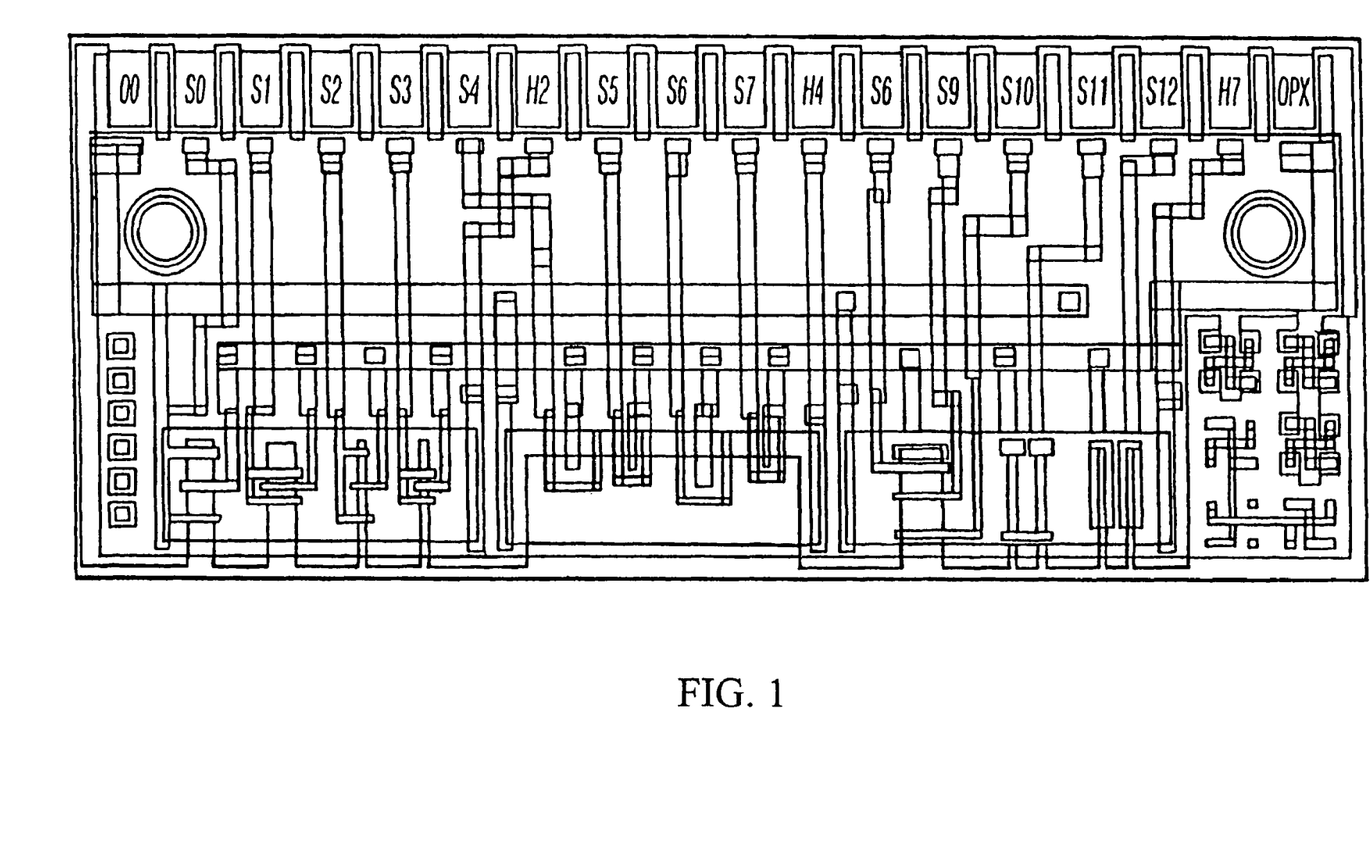
FIG. 1 shows a gas sensor chip which may be utilized as the sensor for the present invention.

Certain extremely sensitive, commercial off-the-shelf (COTS) electronic noses 10, such as those provided by Cyrano Sciences, Inc. ("CSI") (e.g., CSI's Portable Electronic Nose and CSI's Nose-Chip™ integrated circuit for odor-sensing—U.S. Pat. No. 5,945,069—FIG. 1), are preferred in the present invention to monitor the exhaled breath from a patient to detect medication dosing. These devices offer minimal cycle time, can detect multiple odors, can work in almost any environment without special sample preparation or isolation conditions, and do not require advanced sensor design or cleansing between tests.

Other technologies and methods are contemplated herein for detection of markers. For example, a patient's breath can be captured into a container (vessel) for later analysis at a central instrument such as a mass spectrometer.

The present invention will determine if a patient has taken the prescribed drug at the appropriate time and at the prescribed dosage by monitoring and analyzing the exhaled gases with the electronic nose. In a preferred embodiment, the device of the present invention is designed so that patients can exhale via the mouth or nose directly into the device. The device is designed to detect the presence of medications and/or harmless olfactory markers added to medication (discussed hereinafter).

Another preferred electronic nose technology of the present invention comprises an array of polymers, for example, 32 different polymers, each exposed to a marker (e.g., odor). Each of the 32 individual polymers swells differently to the odor creating a change in the resistance of that membrane and generating an analog voltage in response to that specific odor ("signature"). The normalized change in resistance can then be transmitted to a processor to identify the type, quantity, and quality of the odor based on the pattern change in the sensor array. The unique response results in a distinct electrical fingerprint that is used to characterize the odor. The pattern of resistance changes of the array is diagnostic of the sample, while the amplitude of the pattern indicates the concentration of the sample.

The responses of the electronic nose to specific odors can be fully characterized using a combination of conventional gas sensor characterization techniques. For example, the sensor can be attached to a computer. Marker analysis results can be displayed on the computer screen, stored, transmitted, etc. A data analyzer can compare a pattern of response to previously measured and characterized responses from known markers. The matching of those patterns can be performed using a number of techniques, including neural networks. By comparing the analog output from each of the 32 polymers to a "blank" or control odor, for example, a neural network can establish a pattern which is unique to that marker and subsequently learns to recognize that marker. The particular resistor geometries are selected to optimize the desired response to the particular marker being sensed. The electronic nose of the present invention is preferably a self-calibrating polymer system suitable for liquid or gas phase biological solutions for a variety of medications simultaneously.

The electronic nose of the present invention might include integrated circuits (chips) manufactured in a modified vacuum chamber for Pulsed Laser Deposition of polymer coatings. It will operate the simultaneous thin-film deposition wave detection and obtain optimum conditions for high sensitivity of SAW sensors. The morphology and microstructure of biosensor coatings will be characterized as a function of process parameters.

The electronic nose used in the present invention will preferably be modified so that patients can exhale directly into the device. For example, a mouthpiece or nosepiece will be provided for interfacing a patient with the device to readily transmit the exhaled breath to the sensor (See, e.g., U.S. Pat. No. 5,042,501). The output from the neural network of the modified electronic nose should be similar when the same patient exhales directly into the device and when the exhaled gases are allowed to dry before they are sampled by the electronic nose.

The humidity in the exhaled gases represents a problem for certain electronic nose devices (albeit not SAW sensors) which only work with "dry" gases. When using such humidity sensitive devices, the present invention will adapt such electronic nose technology so that a patient can exhale directly into the device with a means to dehumidify the samples. This will be accomplished by including a commercial dehumidifier or a heat moisture exchanger (HME), a device designed to prevent desiccation of the airway during ventilation with dry gases. Alternatively, the patient may exhale through their nose which is an anatomical, physiological dehumidifier to prevent dehydration during normal respiration.

Medication Markers

Upon ingestion of a drug with or without an olfactory coating or additive (see herein), detection can occur under three distinct circumstances. In one, the drug and/or the additive or coating can "coat" or persist in the mouth, esophagus and/or stomach upon ingestion and be detected upon exhalation (similar to the taste or flavor that remains in the mouth after eating a breath mint). In a second instance, the olfactory coating or additive (or the drug) may react in the mouth or stomach with acid or enzymes to produce or liberate the marker that can then be detected with a "burp" or upon exhalation. Thirdly, the drug and/or marker additive can be absorbed in the gastrointestinal tract and be excreted in the lungs (i.e. alcohol is rapidly absorbed and detected with a Breathalyzer). Generally, a non-toxic marker (that can be detected by its chemical or physical properties) added to the medication itself or to the pill or its coating or to the solution of suspension of the medication or taken separately in some form with the medication will provide a method to determine if the drug was taken as prescribed.

While detection is possible by all three mechanisms, drug excretion from the lungs after oral ingestion usually takes longer. Rapid detection after ingestion is preferable so that the patient does not have to wait to perform the test after taking the drug.

However, there may be instances where detection after excretion from the lungs is preferable. This may be the case when an marker or olfactory marker is added to a medication that is given by the intravenous route. Under these circumstances, excretion may occur rapidly since intravenously injected medications pass rapidly to the lungs and can be excreted.

Thus, when a drug is ingested by a patient, the preferred embodiment of the invention detects the presence of that drug almost immediately in the exhaled breath of the patient (or possibly by requesting the patient to deliberately produce a burp) using the electronic nose. Certain drug compositions might not be detectable in the exhaled breath. Others might have a coating to prevent the medication from dissolving in the stomach. In both instances, as an alternate embodiment, a non-toxic olfactory marker (e.g., volatile organic vapors) added to the coating of the pill or in a separate fast dissolving compartment in the pill or the solution (if the medication is in liquid or suspension form) will provide a method to determine if the drug was taken as prescribed. Any number of benign compounds could be used as olfactory markers. Preferably the marker substance will coat the oral cavity or esophagus or stomach for a short while and be exhaled in the breath or in a burp. The electronic nose will determine their presence as well as their concentration. For pills, capsules, and fast-dissolving tablets the markers can be applied as coatings or physically combined or added to the medication. Markers can also be included with liquid medications and inhalers or other dosing means. In use, the electronic nose of the present invention will identify predetermined non-toxic olfactory markers as well as those drugs that can be directly detected without olfactory markers. The electronic noses will not only detect different drugs but also drug concentrations.

Preferably, in operation, the electronic nose will be used to identify a baseline marker spectrum for the patient prior to ingestion of the medication, if necessary. This will prove beneficial for the detection of more than one drug if the patient is required to ingest more than one drug at a time and possible interference from different foods and odors in the stomach, mouth, esophagus and lungs.

The substances referred to as "olfactory markers" herein are detected by their physical and/or chemical properties, which does not preclude using the medication itself as its own marker. Preferable markers include, but are not limited to, the following: trans-Anethole (1-methoxy-4-propenyl benzene)—anise; Benzaldehyde (benzoic aldehyde)—bitter almond; Butyl isobutyrate (n-butyl 2, methyl propanoate)—pineapple; Cinnamaldehyde (3-phenylpropenal)—cinnamon; Citral (2-trans-3,7-dimenthyl-2,6-octadiene-1-al)—citrus; Menthol (1-methyl-4-isopropylcyclohexane-3-ol)—menthol; and alpha-Pinene (2,6,6-trimethylbicyclo-(3,1,1)-2-heptene)—pine. These markers are preferred since they are used in the food industry as flavor ingredients and are permitted by the Food and Drug Administration as indicated in the Code of Federal Regulations, Chapter 21, et. sec. Moreover, these markers are classified "generally recognized as safe" by the Flavor and Extract Manufacturer's Association. These markers are also all natural products and single individual compounds, not mixtures, to enhance detection and represent a variety of chemical structures to enhance differentiation in detection devices. They are generally poorly soluble in water which enhances their volatility and detection in the breath.

Obviously, the number of marker substances that could be used is vast (Reference: Fenaroli's Handbook of Flavor Ingredients, $3^{rd}$ edition, CRC Press, Boca Raton, 1995) and use of such other applicable markers is contemplated herein.

To effectively use the olfactory markers, preferably, the medication (e.g., capsules, tablets, gel-caps) is coated with a known marker substance along with rapidly dissolving glucose and/or sucrose (i.e., the pill is coated with the marker in air-flocculated sugar crystals). This would stimulate salivation and serve to spread the marker around the oral cavity, enhancing the lifetime in the cavity. Since the throat and esophagus are also coated with the marker as the medication is swallowed, detection is further enhanced.

Preferably the device will utilize predetermined signature profiles of specific drugs, classes of drugs, and/or selected markers. The markers could be used for specific drugs or for a class of drugs. For example, a patient may be taking an antibiotic, an antihypertensive agent, and an anti-reflux drug. One marker could be used for antibiotics as a class, or for subclasses of antibiotics, such as erythromycins. Another marker could be used for antihypertensives as a class, or for specific subclasses of antihypertensives, such as calcium channel blockers. The same would be true for the anti-reflux drug. Furthermore, combinations of marker substances could be used allowing a rather small number of markers to specifically identify a large number of medications.

Figure 2:
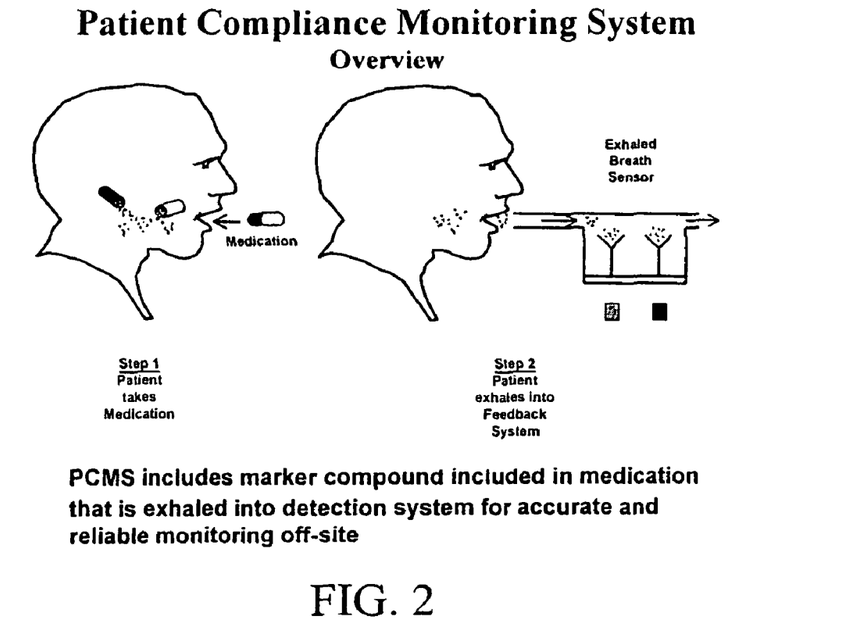
FIG. 2 shows an overview of the preferred steps of the method of the present invention.
Figure 3:
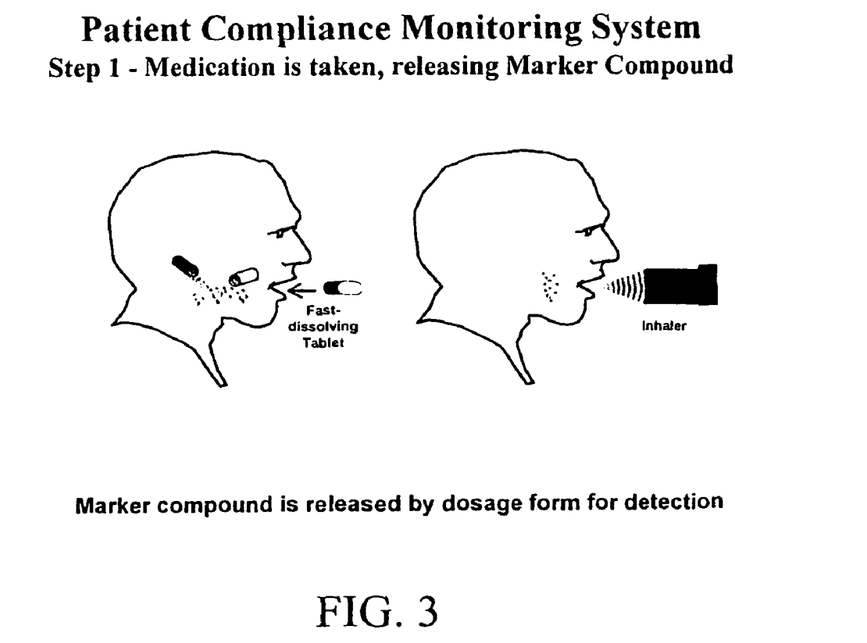
FIG. 3 shows the patient taking medication with a marker which is released for detection.
Figure 4:
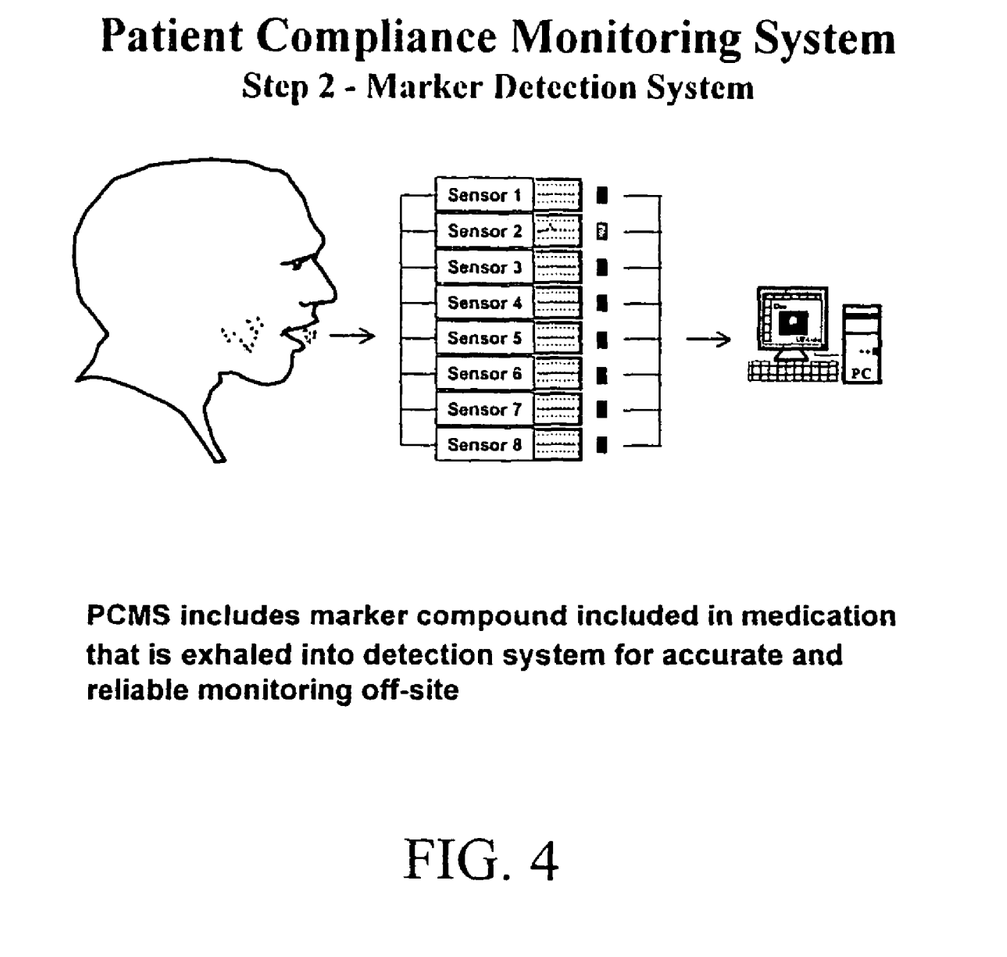
FIG. 4 shows the preferred marker detection system utilizing sensor technology which can communicate with a computer for proximate or remote monitoring.

When the drugs or drugs coated with selected markers are taken (FIG. 2), the drugs are dissolved in the mouth (or digested in the stomach, transmitted to the lungs, etc.). The electronic nose can then detect the marker from the drugs or drugs coated with selected markers when the patient exhales (FIGS. 2-4) to confirm that the medication was taken on a dose by dose basis. The electronic nose can record and/or transmit the data sensed from the patient's breath for monitoring purposes.

While the primary goal of the invention is to improve and document medication compliance in motivated, responsible (albeit occasionally forgetful) individuals, there is a small minority of patients who intentionally do not take their medications, or whose failure to take their medication can result in a public health crisis (i.e. the spread of drug resistant tuberculosis). As a further guarantee that these individuals do not use deceptive practices to "fool" the sensors (i.e. dissolving the tablet or capsules in a small amount of water to release the marker), a pressure sensor can be incorporated into the detector to document that the patient is actually exhaling through the device. A flow restrictor can be incorporated which increases the resistance to exhalation. By the simple addition of a pressure transducer to the system, a pressure change from baseline can be measured during exhalation. Additionally, a number of detectors are available (i.e. end-tidal carbon dioxide monitors) that can be added to the device for use in environments where deception may be likely (i.e. institutions and prisons) and the consequences severe.

Additional embodiments are also envisioned herein. Pulmonary delivery of medications is well known, especially for conditions such as asthma and chronic obstructive pulmonary disease. In these instances, medication (i.e. corticosteroids, bronchodilators, anticholenergics, etc.) is often nebulized or aerosolized and inhaled through the mouth directly into the lungs. This allows delivery directly to the affected organ (the lungs) and reduces side effects common with enteral (oral) delivery. Metered dose inhalers (MDIs) or nebulizers are commonly used to deliver medication by this route. Recently dry powder inhalers have become increasingly popular, as they do not require the use of propellants such as CFCs. Propellants have been implicated in worsening asthma attacks, as well as depleting the ozone layer. Dry power inhalers are also being used for drugs that were previously given only by other routes, such as insulin, peptides, and hormones.

Olfactory markers can be added to these delivery systems as well. Since the devices are designed to deliver medication by the pulmonary route, the sensor array can be incorporated into the device and the patient need only exhale back through the device for documentation to occur.

Lastly, devices are available to deliver medication by the intranasal route. This route is often used for patients with viral infections or allergic rhinitis, but is being increasing used to deliver peptides and hormones as well. Again, it would be simple to incorporate a sensor array into these devices, or the patient can exhale through the nose for detection by an marker sensing system.

The electronic nose and/or computer communicating therewith (FIG. 4) can also notify the medical staff and/or the patient to any irregularities in dosing, dangerous drug interactions, and the like. This system will enable determination as to whether a patient has taken the prescribed drug at the appropriate time and at the prescribed dosage. The device could also alert the patient that it is time to take their medications.

Remote Communication System

A further embodiment of the invention includes a communications device in the home (or other remote location) that will be interfaced to the electronic nose. The home communications device will be able to transmit immediately or at prescribed intervals directly or over a standard telephone line (or other communication means) the data collected by the compliance monitoring device. The communication of the data will allow the physician to be able to remotely verify if the patient took the prescribed drug at the prescribed time and dose. The data transmitted from the home can also be downloaded to a computer where the prescribed drug regimen is stored in a database, and any deviations within limits from the prescribed drug regimen would be automatically flagged (e.g., alarm) so that a home care nurse could telephone the patient and inquire about the reasons for deviating from the prescribed drug regimen.

It should be understood that the examples and embodiments described herein are for illustrative purposes only and that various modifications or changes in light thereof will be suggested to persons skilled in the art and are to be included within the spirit and purview of this application and the scope of the appended claims. Specifically, the marker detection method of the present invention is intended to cover detection not only through the exhalation by a patient with a device utilizing electronic nose technology, but also other suitable technologies, such as gas chromatography, transcutaneous/transdermal detection, semiconductive gas sensors, mass spectrometers, IR or UV or visible or fluorescence spectrophotometers. The invention also includes marker detection not only through a patient's exhaled breath, but also through sweat, saliva, urine, mucous, hair, nails, tears, and other bodily discharge of the patient.

We claim:

1. A method to determine whether a patient has taken a medication, comprising
    providing to a patient a medication comprising a combination of at least one active therapeutic agent and an odorous compound or olfactory marker, which is not chemically part of the active therapeutic agent itself, detectable in gaseous exhaled breath, the combination to be taken by the patient as a result of the patient's own actions;
    obtaining a sample of the patient's gaseous exhaled breath;
    analyzing the sample of the patient's breath utilizing an electronic nose to detect said odorous compound or olfactory marker detectable in gaseous exhaled breath to ascertain the presence or absence of said marker in the patient's breath, where the presence of the odorous compound or marker is an indication that the patient has taken the medication at a prescribed time and in a prescribed dosage and the absence of the odorous compound or marker is an indication that the patient has not taken the medication at all or at a prescribed time or in a prescribed dosage; wherein the medication is to be taken by volitional patient action at specified times and in prescribed dosage; and,
    based on the analysis, determining whether the patient has taken the medication or not at a prescribed time or in a prescribed dosage.

2. The method of claim 1 wherein the sample of the patient's breath is analyzed to ascertain the presence or absence of said odorous compound or olfactory marker by said electronic nose which employs sensor technology selected from the group consisting of semiconductor gas sensor technology and conductive polymer gas sensor technology.

3. The method of claim 2 wherein if the odorous compound or olfactory marker is present in the sample of the patient's breath, the sensor technology produces a unique electronic fingerprint which is an indication of the presence of the odorous compound or olfactory marker in the patient's breath.

4. The method of claim 1 wherein the odorous compound or olfactory marker is selected from trans-Anethole (1-methoxy-4-propenyl benzene)—anise; Benzaldehyde (benzoic aldehyde)—bitter almond; Butyl isobutyrate (n-butyl 2, methyl propanoate)—pineapple; Cinnamaldehyde (3-phenylpropenal)—cinnamon; Citral (2-trans-3,7-dimenthyl-2,6-octadiene-1-al)—citrus; Menthol (1-methyl-4-isopropylcyclohexane-3-ol)—menthol; and alpha-Pinene (2,6,6-trimethylbicyclo-(3,1,1)-2-heptene)—pine.

5. The method of claim 1 wherein the sample of the patient's breath is analyzed to ascertain the presence or absence of said odorous compound or olfactory marker by a spectrophotometer.

6. The method of claim 1 wherein the sample of the patient's breath is analyzed to ascertain the presence or absence of said odorous compound or olfactory marker by a mass spectrometer.

7. The method of claim 1 wherein the odorous compound or olfactory marker is an additive combined with the medication.

8. The method of claim 1 wherein the odorous compound or olfactory marker is provided with the medication in the form of a coating on the medication.

9. The method of claim 8 wherein a substance to stimulate salivation is included with the marker.

10. The method of claim 1 wherein said providing comprises providing the odorous compound or olfactory marker with said medication as a liquid.

11. The method of claim 1 wherein said providing comprises providing the odorous compound or olfactory marker with said medication for the patient to take via the lungs.

12. The method of claim 1 wherein said providing comprises providing the odorous compound or olfactory marker with said medication for the patient to take-intranasally.

13. The method of claim 1 wherein said providing comprises providing the odorous compound or olfactory marker with said medication for the patient to take intravenously.

14. The method of claim 1 further comprising the step of recording results regarding the presence or absence of the odorous compound or olfactory marker as provided from the analysis of the sample of the patient's breath.

15. The method of claim 14, further comprising the step of transmitting the results from the analysis of the sample of the patient's breath to an individual interested in the results.

16. The method of claim 1 where the analysis of the sample of the patient's breath includes comparing any odorous compound or olfactory marker sensed in the sample of the patient's breath with a predetermined signature profile of a specific odorous compound or olfactory marker.

17. The method of claim 16 wherein the predetermined signature profile of a specific odorous compound or olfactory marker is associated with a specific drug.

18. The method of claim 16 wherein the predetermined signature profile of a specific odorous compound or olfactory marker is associated with a class of drugs.

19. The method of claim 1 further comprising the step of capturing the sample of the patient's breath in a vessel prior to analysis.

20. The method of claim 1 further comprising the step of dehumidifying the sample of the patient's breath prior to analysis.

21. The method of claim 1 wherein the odorous compound or olfactory marker is not detectable unless it first reacts with enzymes in the patient's mouth.

22. The method of claim 1 wherein the odorous compound or olfactory marker is not detectable unless it first reacts with acids in the patient's stomach.

23. The method of claim 1 wherein the odorous compound or olfactory marker is not detectable unless it first is absorbed in the patient's gastrointestinal tract and then is, at least partially, excreted from the lungs.

24. The method of claim 1, further comprising: if it is determined that the patient did take the medication, analyzing the sample of the patient's breath to ascertain the concentration of said odorous compound or olfactory marker in the patient's breath.

25. The method of claim 1 further comprising identifying a baseline odorous compound or olfactory marker spectrum for the patient at a time prior to a time at which it is desired to ascertain whether a patient has taken a medication.

26. A method of producing medication which is detectable as an indication of patient compliance in taking the medication comprising the steps of:
    identifying an odorous compound or detectable olfactory marker substance detectable in gaseous exhaled breath, and
    combining a medication with said odorous compound or detectable olfactory marker substance, wherein said medication is to be taken by volitional patient action at specified times whereby subsequent analysis of the patient's breath will confirm the presence or absence of said odorous marker or detectable olfactory marker substance and thus indicate whether the patient has complied in taking said medication at a specified time and at a specified dosage, wherein said combining comprises physically combining said odorous compound or detectable olfactory marker substance with said medication for administration in the form of pills, capsules, or fast-dissolving tablets, wherein said odorous compound or olfactory marker substance is present in a separate fast-dissolving compartment in the pill, capsule or tablet.

27. The method of claim 1 wherein said providing comprises providing the odorous compound or olfactory marker with a medication for the patient to take transdermally.

28. The method of claim 1 wherein the odorous compound or olfactory marker is a combination of odorous compounds or olfactory markers combined as an additive with the medication.

29. The method of claim 1 wherein more than one therapeutically active agent is included in the medication.

30. The method of claim 1 wherein said odorous compound or olfactory marker is a Generally Recognized as Safe compound.

31. The method of claim 1 wherein the patient is alerted as to the results of said method and if the result of said method indicates non-compliance, this can be remedied.

32. The method of claim 1 wherein said obtaining a sample of the patient's gaseous exhaled breath and said analyzing the sample of the patient's breath utilizing said electronic nose to detect said odorous compound or olfactory marker occurs at said patient's home or other remote location and wherein the results of said obtaining and said analyzing are transmitted via a communication means to a computer for compliance monitoring by medical staff.

* * * * *